(12) United States Patent
Riemann et al.

(10) Patent No.: US 9,074,259 B2
(45) Date of Patent: Jul. 7, 2015

(54) USE OF GENETIC MODIFICATIONS IN HUMAN GENE CHK1 WHICH CODES FOR CHECKPOINT KINASE 1

(71) Applicant: UNIVERSITAT DUISBURG-ESSEN, Essen (DE)

(72) Inventors: Kathrin Riemann, Mittelbiberach (DE); Winfried Siffert, Essen (DE)

(73) Assignee: UNIVERSITAT DUISBURG-ESSEN, Essen (DE)

( * ) Notice: Subject to any disclaimer, the term of this patent is extended or adjusted under 35 U.S.C. 154(b) by 283 days.

(21) Appl. No.: 13/666,606

(22) Filed: Nov. 1, 2012

(65) Prior Publication Data

US 2013/0189676 A1    Jul. 25, 2013

Related U.S. Application Data

(63) Continuation of application No. 12/312,474, filed as application No. PCT/EP2007/062519 on Nov. 19, 2007, now abandoned.

(30) Foreign Application Priority Data

Nov. 17, 2006    (DE) .......................... 10 2006 054 292

(51) Int. Cl.
  *C12Q 1/68* (2006.01)
(52) U.S. Cl.
  CPC ............ *C12Q 1/6886* (2013.01); *C12Q 1/6883* (2013.01); *C12Q 2600/106* (2013.01); *C12Q 2600/118* (2013.01); *C12Q 2600/172* (2013.01)
(58) Field of Classification Search
  None
  See application file for complete search history.

(56) References Cited

U.S. PATENT DOCUMENTS

| | | | |
|---|---|---|---|
| 2003/0087847 A1 | 5/2003 | Jarvis et al. | |
| 2006/0147936 A1 | 7/2006 | Frey et al. | |
| 2008/0020385 A1 | 1/2008 | Frey et al. | |

FOREIGN PATENT DOCUMENTS

| WO | WO 99/11795 A | 3/1999 |
|---|---|---|
| WO | WO 2005/118845 A | 12/2005 |

OTHER PUBLICATIONS

Riemann et al. (The FASEB Journal, 2007:21:567.5; published Apr. 2007).*
Carrassa et al. (Cell Cycle 2:6, 604-609; Nov./Dec. 2003).*
Hegele. Arterioscler Thromb Vasc Biol 2002;22;1058-1061.*
Zill et al.Molecular Psychiatry (2004) 9, 1030-1036.*
Riemann, et al., "Promoter polymorphisms in the gene encoding checkpoint kinase 1 are associated with survival in cancer". FASEB Journal, 21, No. Apr. 5, 2007, p. A418. Abstract 567.5, 1 page.
Riemann, et al., "CHK1 promoter polymorphism predicts survival in cancer", ASCO Annual Meeting 2008. Online at www.abstract.asco.org/AbstView__55__30685.html, 2 pages.
Carrassa, et al., "Characterization of the 5'Flanking Region of the Human Chk1 Gene", Cell Cycle, 2:6, 604-609, Nov./Dec. 2003.
Hegele, "SNP Judgments and Freedom of Association", Arterioscler Thromb Vasc Biol, 2002, 22, pp. 1058-1061.
Zill, et al., "SNP haplotype analysis of a novel tryptophan hydroxylase isoform (TPH2) gene provide evidence for association with major depression", Molecular Psychiatry, (2004)9, 1030-1036.
PCT Notification Concerning Transmittal of International Preliminary Report on Patentability, dated Jun. 18, 2009 issued by the International Bureau of WIPO. Connection with PCT International Patent Application No. PCT/EP2007/062519, 7 pages.
Stambrook, "Haplotypes, SNPs and disease", Mutation Research, 564 (1-2):407-415, 2004.

* cited by examiner

*Primary Examiner* — Juliet Switzer
(74) *Attorney, Agent, or Firm* — Fanelli Haag PLLC

(57) ABSTRACT

The invention relates to an in vitro method for predicting disease risks, progression of diseases, drug risks, success of treatment and for finding drug targets by looking for one or more genetic modifications in the promoter region of the CHK1 (CHEK1) gene on human chromosome 11q23, the genetic modifications being a substitution thymine for guanine in position −1143 in the promoter of CHK1, of thymine for cytosine in position −1400, a substitution of cytosine for thymine in position −1453 or an insertion of one cytosine in position −1454 and the genetic modifications being detected individually or in any combinations by way of known methods.

5 Claims, 11 Drawing Sheets

Figure 7

```
-1,527  aaaaagaccg ggctgaagta aagcattgtt ttggagctgg ttcacagaaa

-1,477  aaaggcaaaa ctggttatcc tgac-Ttcaag ctccaacata aactgctcgc -
1453T>C
                             bZIP910 CC                               -
1454insC
-1,427  tttctccggg aaacttgccc cgccacaCac acttgactgc gtggccagtt -
1400C>T
                        CF2-II T
-1,377  ctttgaagc ctctcgctcc aaacacggag ttcctcccat ttcttcacag -1,227  agtcctgtcc ggtggcctca cgcaggtggc ggtgcagcct ttcaggccca -1,177  gagcggccag gagcgaagcc cgcagcccg cctgGaagcg cagcgggtc -
1143G>T
                                        E74A T
-1,127  ggtcgcgcgc ccctgagget tggaggcctg ggcttcccc agcagcgctc
```

Figure 8

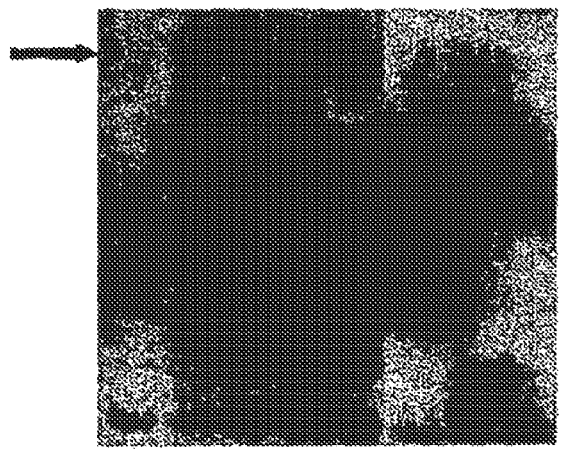

SEQUENCE LISTING

```
<160> NUMBER OF SEQ ID NOS: 1

<210> SEQ ID NO 1
<211> LENGTH: 350
<212> TYPE: DNA
<213> ORGANISM: Homo sapiens

<400> SEQUENCE: 1
aaaaagaccg ggctgaagta aagcattgtt ttggagctgg ttcacagaaa aaaggcaaaa      60
ctggttatcc tgacttcaag ctccaacata aactgctcgc tttctccggg aaacttgccc     120
cgccacacac acttgactgc gtggccagtt ctttcgaagc ctctcgctcc caacacggag     180
ttcctcccat ttcttcacag agtcctgtcc ggtggcctca cgcaggtggc ggtgcagcct     240
ttcaggccca gagcggccag gagcgaagcc cgcagccccg cctggaagcg cagcgcggtc     300
ggtcgcgcgc ccctgaggct tggaggcctg ggcttccccc agcagcgctc                350
```

USE OF GENETIC MODIFICATIONS IN HUMAN GENE CHK1 WHICH CODES FOR CHECKPOINT KINASE 1

CROSS-REFERENCE TO RELATED APPLICATIONS

The present application is a continuation of U.S. application Ser. No. 12/312,474, filed Jan. 287, 2010, which is a national stage entry under 35 U.S.C. §371 of PCT International Application No. PCT/EP2007/062519, filed Nov. 19, 2007, which claims priority to German Patent Application No. 102006054292.4, filed Nov. 17, 2006, the disclosures of each of which are incorporated by reference herein in their entireties.

The instant application contains a Sequence Listing which has been submitted via EFS-Web and is hereby incorporated by reference in its entirety. Said ASCII copy, created on Nov. 1, 2012, is named 0051_0082_US2_Sequence_Listing.txt and is 973 bytes in size.

TECHNICAL FIELD OF THE INVENTION

The invention relates to an in vitro method for predicting disease risks, progression of diseases, drug risks and for finding drug targets.

TECHNICOLOGICAL BACKGROUND OF THE INVENTION

Cancer cells are characterized by loss of contact inhibition and uncontrolled cell growth. Such modifications are triggered spontaneously or by noxae, co-called cancerogenes, which damage the genetic make-up. Such noxae include many chemicals, tobacco smoke, but also UV light. Besides that, genetic factors play a prominent role in the formation of cancer. Characteristic for cancer cells, beside their uninhibited growth, is also the tendency to form metastases in other organs.

It is of exceedingly high medical relevance to define prognosis factors for the progression of cancers, which provide information about the response to certain forms of treatment or are generally predictive for the occurrence of metastases, tumor progression and survival. So far, prognosis factors generally known to the person skilled in the art are used in medicine. These include, for example, the size of the tumor, its penetration depth into the surrounding tissue, cross-organ growth, the penetration into blood or lymphatic vessels or into lymph nodes, as well as the degree of differentiation of the tumor cells. In addition, some relatively unspecific serological markers exist.

The cell cycle of eukaryotic cells is generally subdivided into four phases: the G1-phase, in which the preparation for replication takes place, the S-phase, in which the DNA is synthesized and the actual cell functions take place, the G2-phase, in which the preparation for mitosis takes place, and the M-phase, the mitosis (FIG. 1). In addition, differentiated cells, which no longer divide, are described as being in the G0-phase. This organizational principle though is functional, but on closer inspection it becomes clear that the cell cycle is far more complex. Numerous processes must be initiated and activated, individual components joined and various cascades coordinated. For this reason, diverse control mechanisms exist, which ensure that any processes within the cell cycle are completed correctly. These control mechanisms are designated as "checkpoints[1]". These are not fixedly defined points, as the word itself implies, but a reaction cascade, which can be initiated under certain circumstances.

[1] Original definition (according to Weinert et al., The RAD9 gene controls the cell cycle response to DNA damage in *Saccharomyces cerevisiae*. 1988, Science 241:317-22): If a process B depends on the completion of a process A, then this dependency is conditional on a checkpoint, unless a mutation can eliminate the dependent relationship.

So far, several cell cycle checkpoints were characterized. The best investigated checkpoints in mammals are shown in FIG. 1. On the one hand, there is the DNA damage checkpoint, which can be activated by a damage of the DNA in different cell cycle phases. This damage can be caused by exogenous causes, like radiation, as well as by endogenous processes, e.g. spontaneous mutations. On the other hand, the replication checkpoint is activated by an incomplete or defective replication of the DNA. The spindle checkpoint monitors the formation of the bipolar spindle, the attachment of the kinetochores and the new formation of the centromere structures.

As long as these processes are not entirely completed or the damage eliminated, the entrance of the cell into the next cell cycle phase is inhibited to ensure that the genomic integrity of the cell is maintained (Elledge, S. J., Cell cycle checkpoints: preventing an identity crisis. 1996, Science 274:1664-72).

The most important task of a cell is to maintain genomic identity. Checkpoint kinase 1 is involved in essential control mechanisms in the cell cycle, which ensure that the transfer of defects to the daughter cell is minimized. The significant CHK1 reaction cascade at the G2/M checkpoint is shown in FIG. 2. The activation of CHK1 takes place due to DNA damages, which are mainly detected by the chromatin-bound Rad17 complex. Thereupon, the Rad17 complex recruits the Rad9-Hus1-Rad1 complex, which together with the ATR-Atrip complex activates CHK1, which is partially present in a chromatin-associated form, by phosphorylation. In that, ATR (Ataxia-telangiectasia- and Rad3-related) represents the most important activating component. It was shown that for the complete activation of CHK1, phosphorylation by the protein Claspin is also required. The activated CHK1 protein migrates from the cell nucleus into the cytoplasm, where in its turn it activates CDC25C (cell division cycle 25C) by phosphorylation. This process, on the other hand, enables the 14-3-3 protein (tyrosine 3-monooxygenase/tryptophan 5-monooxygenase activation protein) to bind to CHK1, so that it can return into the nucleus and remains there. In this manner, CDC2 (cell division controller 2) as well as the cyclin B complex are inhibited, which inhibits the entrance into mitosis. Subsequently, the DNA repair system can be initiated to eliminate the DNA damage (Jiang et al., Regulation of Chk1 includes chromatin association and 14-3-3 binding following phosphorylation on Ser345. 2003, J. Biol. Chem. 278: 25207-17; Jeong et al., Phosphorylated claspin interacts with a phosphate-binding site in the kinase domain of Chk1 during ATR-mediated activation. 2003, J. Biol. Chem. 278:46782-8).

For CHK1, involvement in a checkpoint in the S-phase could also be verified. Here, upon defective replication, CHK1 is activated by ATM (Ataxia-telangiectasia mutated) by phosphorylation. For this checkpoint, too, additional activation by Claspin is required. The completely activated CHK1 now activates DNA protein kinases, together with which they phosphorylate p53 and thus can increase its activity. CHK1 is likewise able to phosphorylate TLK1 (tousled like kinase 1). This protein plays a decisive role in chromatin condensation, which, however, is inhibited by CHK1 to prevent progression in the cell cycle. Furthermore, CHK1 phosphorylates CDC25A (cell division cycle 25A) and thus initiates its degradation. As a consequence, the CDC protein is

SUMMARY OF THE INVENTION

The invention is therefore based on the object to provide a means, which enables a better prognosis of the natural progression of a cancer and the response to any form of treatment. In particular, this means is to be able to detect those patients, in which increased DNA repair mechanisms aggravate a cancer treatment. The invention is further based on the object to provide a means to generally predict disease risks and progression of diseases, since DNA repair mechanisms are also very important for other diseases.

In particular,
(a) function-modifying genomic polymorphisms in the promoter of the CHK1 gene are to be provided, which either result in the modification of the protein expression or in the modification of the expression of splicing variants, or
(b) which are suited to find and/or validate further polymorphisms or haplotypes in the CHK1 gene,
c) polymorphisms are to be provided, which are suited to generally predict disease risks and progression,
(d) polymorphisms are to be provided, which are suited to generally predict the response to pharmaceuticals and cancer treatments, in particular CHK1 inhibitors, and side-effects,
(e) polymorphisms are to be provided, which are suited to generally predict the effect of other forms of treatment like radiation, warmth, heat, cold, movement.

These objects are solved by an in vitro method for predicting disease risks, progression of diseases, drug risks and for finding drug targets by looking for one or more genetic modifications in the promoter region of the CHK1 (CHEK1) gene on human chromosome 11q23.

PREFERRED EMBODIMENTS OF THE INVENTION

Such polymorphisms are, for example, (−1143)G>T, (−1400)C>T, (−1453)T>C, and (−1454)insC.

The human gene CHK1 is localized on chromosome 11q23 (Accession No. NM_033899 of the Gene Bank of the National Center for Biotechnology information (NCBI)) and codes for a 54 kD protein, which is expressed in the nucleus. At this point, it is to be pointed out that the gene has the designation "CHK1" as well as the designation "CHEK1". In the following, the designation "CHK1" shall be used here. A schematic representation of the gene structure is shown in FIG. 3. The active promoter region of CHK1 has already been characterized. The promoter sequence contains numerous binding sites for the transcription factor E2F1, the binding of which enhances the transcriptional activity. A positive regulation of CHK1 is likewise observed by an isoform of the p53-dependent p73 (Carrassa et al., Characterization of the 5'-flanking region of the human Chk1 gene. 2003, Cell Cycle 2:604-9).

Figure 6:
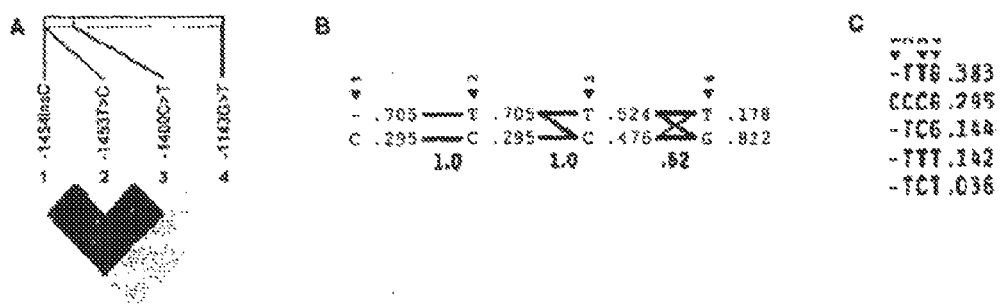

FIG. 6 shows the coupling analyses of the promoter polymorphisms of CHK1 with the program Haploview; A-Graphical representation of the coupling of the polymorphisms among one another. Black squares indicate $r^2=1$, grey squares $r^2<0.5$ and light-grey squares $r^2<0.1$; B-Frequencies and coupling possibilities of the individual alleles; C-Frequencies of the constructed haplotypes; alleles marked with a triangle are designated so-called haplotype-tagging alleles, i.e. these alleles must be determined to determine the respective haplotypes.

FIG. 7 shows putative binding sites for transcription factors in the promoter of the CHK1 gene (SEQ ID NO: 1); the numbers on the left-hand side represent the relation to the ATG.

FIG. 8 shows the result of the Electrophoretic Mobility Shift Assay (EMSA) with constructs containing the various alleles of the −1143G>T polymorphism of CHK1. Following the addition of cell nucleus extract, increased binding of core protein to the "G-construct" can be detected. The binding is specifically inhibited by the presence of a displacing oligonucleotide.

Figure 9:
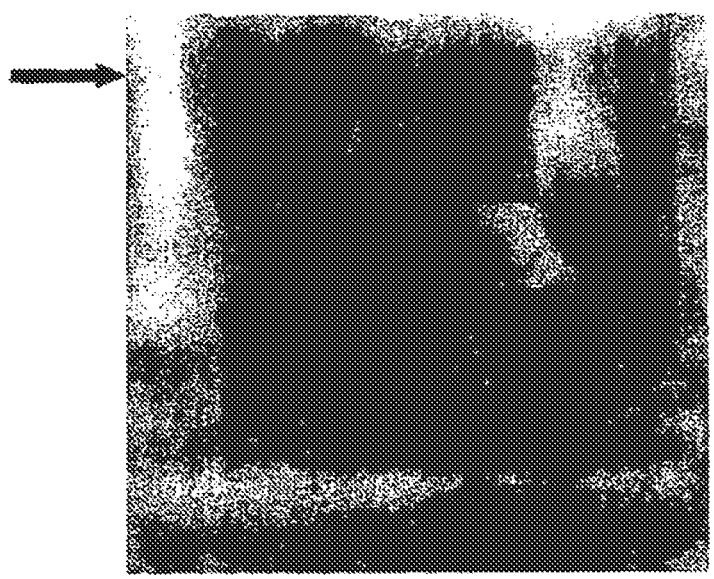

FIG. 9 shows the result of the Electrophoretic Mobility Shift Assay (EMSA) with constructs containing the various alleles of the −1400C>T polymorphism of CHK1. Following the addition of cell nucleus extract, increased binding of core protein to the "T-construct" can be detected. The binding is specifically inhibited by the presence of a displacing oligonucleotide.

Figure 10:
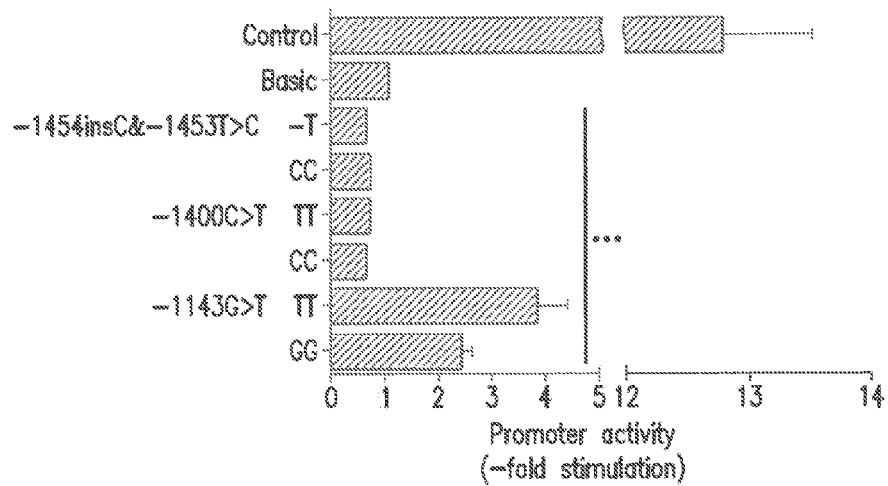

FIG. 10 shows constructs for measuring the genotype-dependent regulatory activity of the promoter polymorphisms after 24 h following the transfection of HELA cells using secreted alkaline phosphatase (SEAP). The activity of the 1143G>T SNP is significantly higher than the activity of the other SNPs. ***: $p<0.001$.

Figure 11:
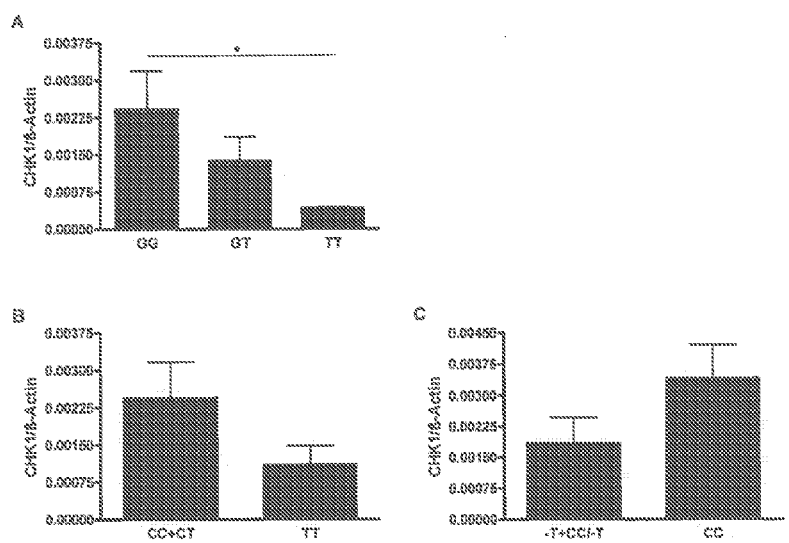

FIG. 11 shows an expression of CHK1 mRNA in urinary bladder carcinoma tissue depending on the alleles of the promoter polymorphisms. Represented is the quotient CHK1/β-actin mRNA. A: −1143G>T, B: −1400C>T, C: −1453T>C and 1454insC; *: $p<0.05$.

Figure 12:
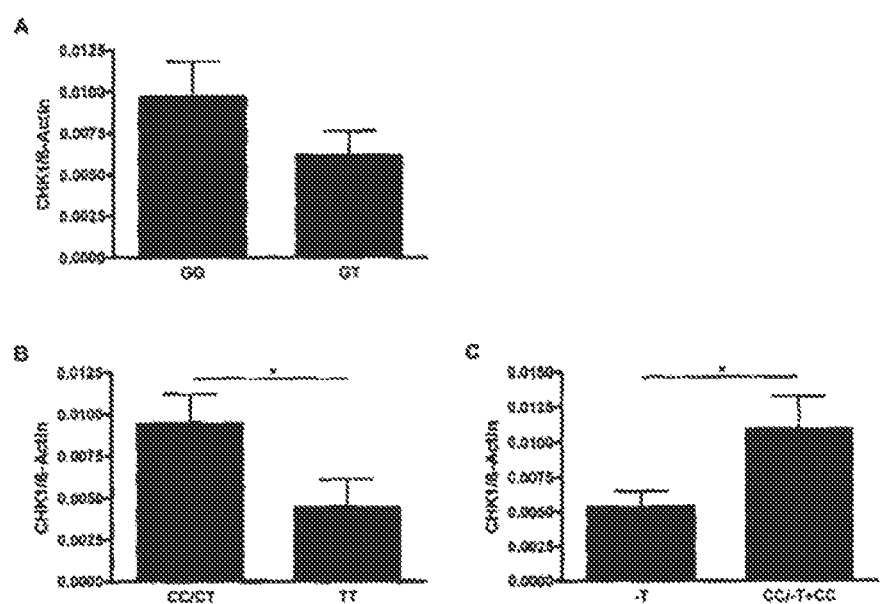

FIG. 12 shows an expression of CHK1 mRNA in colorectal carcinoma tissue depending on the alleles of the promoter polymorphisms. Represented is the quotient CHK1/β-actin mRNA. A: −1143G>T, B: −1400C>T, C: 1453T>C and −1454insC; *: $p<0.05$.

Figure 13:
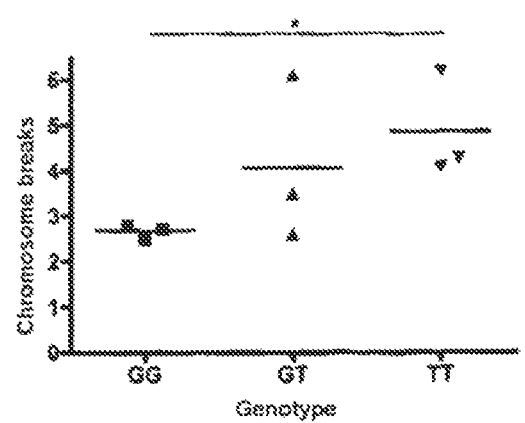
Figure 14:
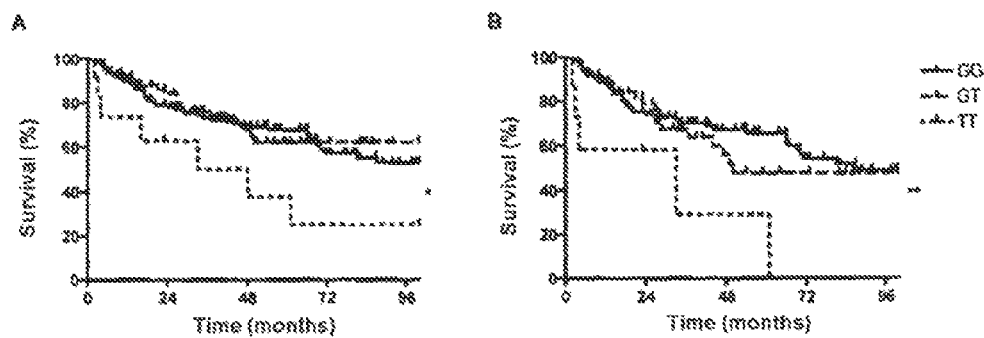
Figure 15:
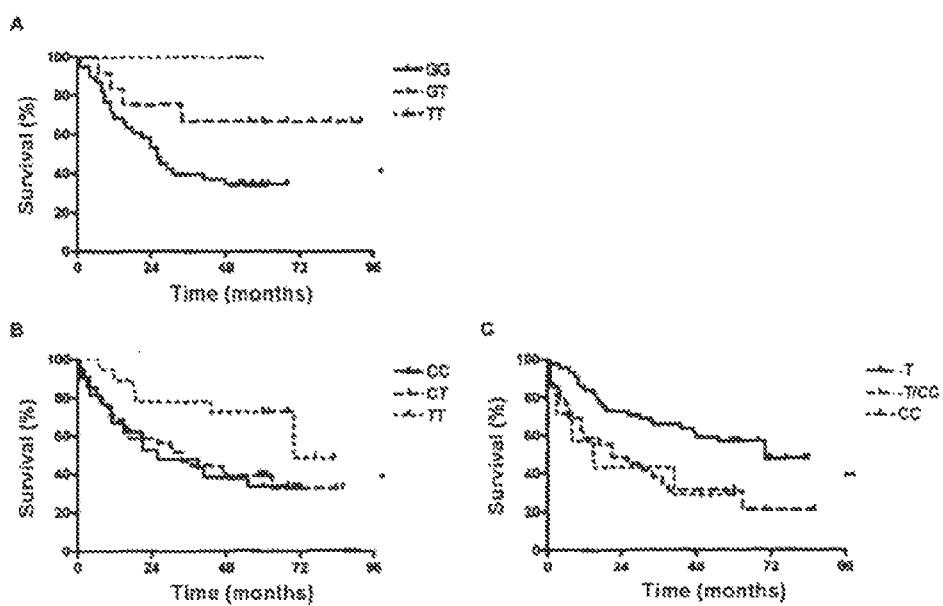

FIG. 13 shows the Kaplan-Meier analysis on the survival of patients with urinary bladder carcinoma depending on the genotype of the −1143G>T polymorphism. A: all patients, B: only patients older than 54 years; *: $p<0.05$, **: $p<0.01$ FIG. 14 shows the Kaplan-Meier analysis on the survival of patients with colorectal carcinoma depending on the genotype of the promoter polymorphisms. A: Dependency on the −1143G>T SNP, B: only patients with colon carcinoma depending on the −1400C>T SNP, C: only patients with colon carcinoma depending on the 1453T>C SNP and −1454insC SNP; *: $p<0.05$, **: $p<0.01$ FIG. 15 shows the Kaplan-Meier analysis on the survival of patients with chronic lymphatic leukemia depending on the genotype of the −1143G>T polymorphism.

Figure 16:
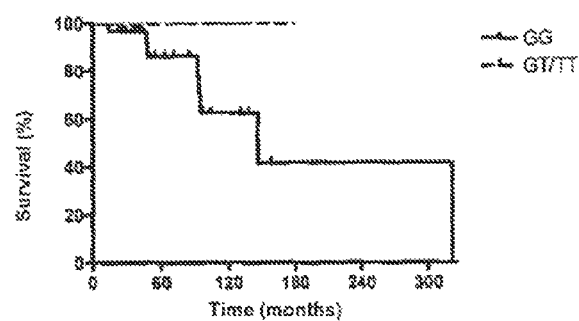

FIG. 16 shows the Kaplan-Meier analysis of patients with melanoma depending on the genotype of the −1400C>T promoter polymorphism; A: Time from initial treatment to start of further treatment; B: Survival; *: $p<0.05$.

Figure 17:
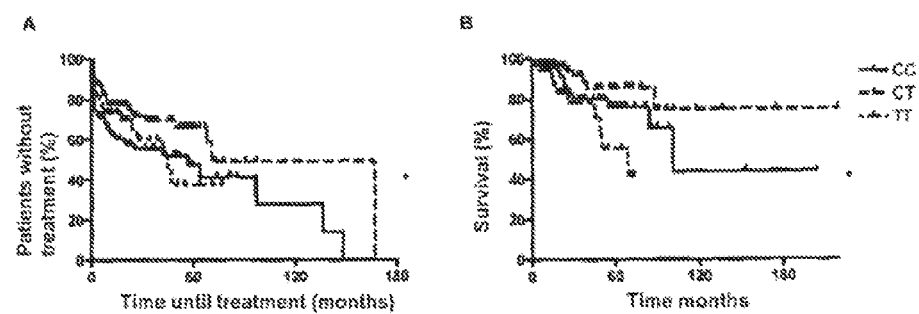

FIG. 17 shows the Kaplan-Meier analysis on the survival of patients with cholangiocellular carcinoma depending on the genotype of the −1400C>T polymorphism; *: $p<0.05$.

Figure 18:
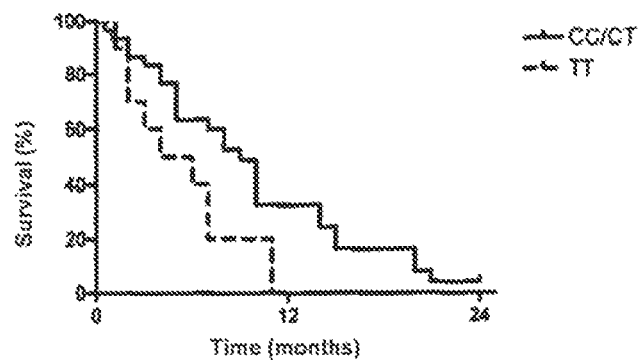

FIG. 18 shows a Kaplan-Meier analysis on the survival of patients with cholangiocellular carcinoma depending on the genotype of the −1400C>T polymorphism. *: p<0.05.

Figure 19:
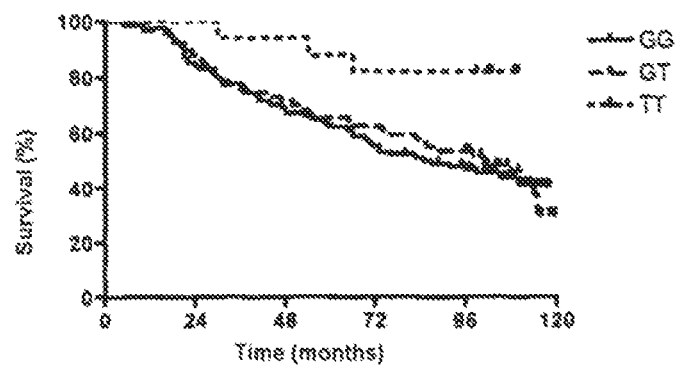

FIG. 19 shows a Kaplan-Meier analysis on the survival of patients with mammary carcinoma depending on the genotype of the −1143G>T polymorphism, *: p<0.05

CHK1 is considered a potential tumor suppressor gene, since a defect in the regulation of the cell cycle results in cumulation of defective DNA and an increased cellular proliferation rate, both of which are characteristics of tumor cells. So far, somatic mutations in this gene could be verified in some patients with sporadic tumors, e.g. stomach and mammary carcinoma as well as microsatellite-instable colorectal tumors showed alterations. Unlike single nucleotide polymorphisms (SNPs), these mutations are, for example, not found in peripheral blood cells in the respective patients. Disease-specific associations for SNPs have not been described yet.

Since checkpoints are involved in many regulatory cascades, they are a suitable target for cancer therapeutic agents. Certain characteristics of the checkpoint proteins contribute to that: (1) the complex signal transduction system of checkpoints offers a multitude of targets, (2) in healthy cells, some checkpoints seem to be relatively insignificant, which highly reduces the toxicity of the inhibitors, (3) the restoration of defective checkpoints could result in a slow-down of the cell growth, (4) as a signal transduction system, checkpoints are subject to adaption, which could be interrupted, and (5) the restoration of affected checkpoints could increase the apoptosis rate of cancer cells and thus increase their sensitivity towards certain substances (Hartwell et al., Cell cycle control and cancer. 1994, Science 266:1821-8).

Contrary to these points, which most likely can be realized via a gene therapy approach, two further characteristics of checkpoints represent simpler realizable targets. Cells with defective checkpoints show a highly increased sensitivity towards radiation and cytotoxic substances. Particularly the loss of CHK1 seems to predispose tumor cells for these types of treatment.

Figure 1:
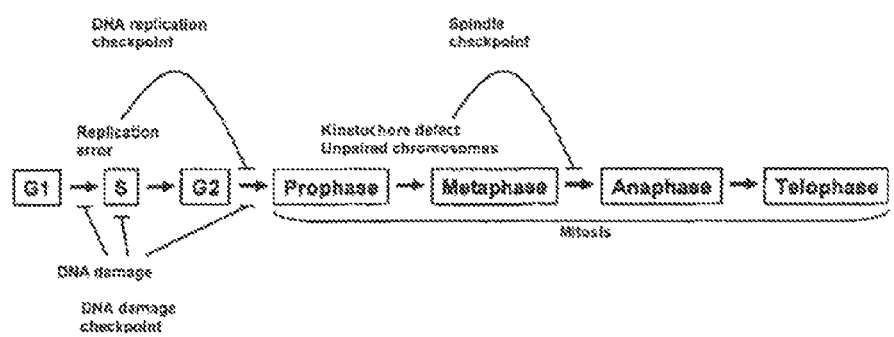
FIG. 1 shows a schematic representation of the cell cycle with the most important checkpoints.
Figure 2:
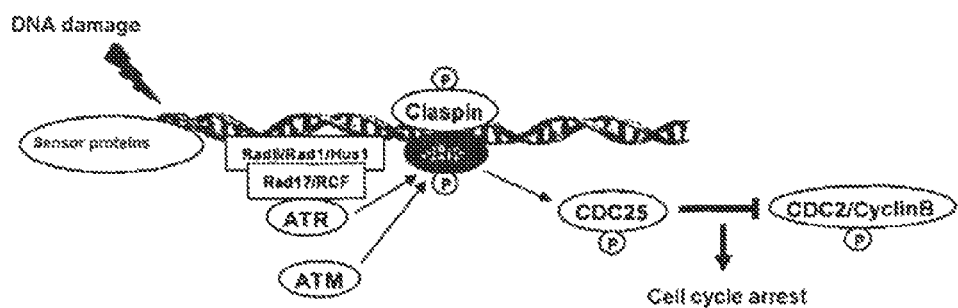
FIG. 2 shows a graphical representation of the reaction cascade at the DNA damage checkpoint.
Figure 3:
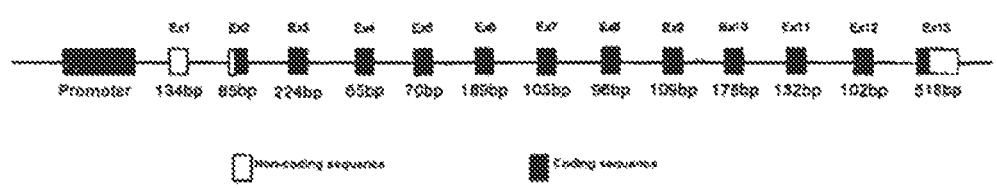
FIG. 3 shows the intron/exon structure of the human gene CHK1 (not to scale).
Figure 4:
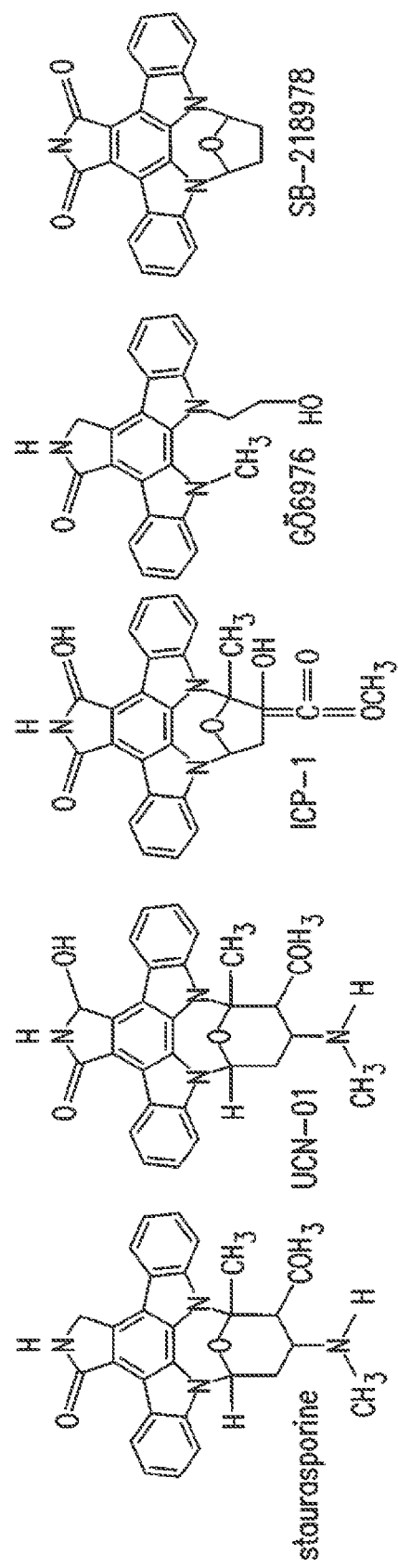
FIG. 4 shows the structural relationship of some CHK1 inhibitors with staurosporine.

Diverse CHK1 inhibitors are already known or have already been developed. Based on staurosporine, originally identified as protein kinase C inhibitor, which likewise is a potent CHK1 inhibitor, various substances were derived. These include, for example, the CHK1 inhibitors UCN-01 (7-hydroxy-staurosporine), Gö6976, SB-218078, ICP-1, XL844, and CEP-3891, which block the G2/M checkpoint (FIG. 4). Furthermore, debromohymenialdisine and the synthetic peptide TAT-S216A can inhibit CHK1 as well as a further checkpoint protein, CHK2. It has to be assumed, that in the near future even far more substances will be available, which inhibit CHK1.

Among the CHK1 inhibitors available so far, UCN-01 (7-hydroxy-staurosporine) is the clinically best characterized substance. UCN-01 has already passed through several clinical phase I studies and is currently tested in phase II. The inhibition or down regulation of CHK1 had a positive effect on the response of cytostatics, like topoisomerase inhibitors, antimitotics and antimetabolites, since due to the lack of CHK1, the toxicity of these chemotherapeutic agents was potentiated especially in aggressive tumors, which even following preceding conventional treatment showed progressive growth. Furthermore, it could be demonstrated that UCN-01 increases the sensitivity towards radiation, whereby CHK1 inhibitors also have potential as radio-sensitizers.

Figure 5:
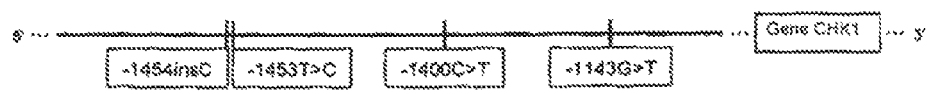
FIG. 5 shows a schematic representation of the polymorphisms in the CHK1 gene (not to scale).

Due to the fundamental significance of CHK1 for the maintenance of genomic integrity, such polymorphisms are suited to generally predict disease risks or progression of diseases in tumor diseases or to predict treatment responses/treatment failure or undesired side-effects for all pharmaceuticals or non-pharmacological treatments, Verification of Polymorphisms in the Promoter of the CHK1 Gene In the promoter region of CHK1, five polymorphisms are known and can be found in generally accessible databases. With systematic sequencing of human DNA samples, three polymorphisms were verified and validated: −1143G>T (rs555752), −1400C>T (rs558351) and −1453T>C (rs1057733) (FIG. 5). For that, gene sequences of the promoter area of CHK1 were amplified using PCR reaction and sequenced with method according to Sanger. The person skilled in the art is familiar with the methods required for that, e.g. deriving primer pairs required for the PCR reaction and selecting sequencing primers. In that, a new polymorphism was found, whereat there is an insertion of one cytosine present (1454insC, no database SNP identification present) at position 1454 in the promoter region (FIG. 5). The numbering of these SNPs takes place in a manner that nucleotide A of the start codon ATG is allocated the number +1. Since according to the convention there is no number 0, the nucleotide located in front of the A of the start codon ATG is allocated number −1.

The verification of these SNPs in terms of their use according to the invention can be executed with any method the person skilled in the art is familiar with, e.g. direct sequencing, PCR with subsequent restriction analysis, reverse hybridization, dot blot or slot blot methods, mass spectrometry, Taqman® or Light-Cycler® technology, Pyrosequencing®, Invader® technology, Luminex methods, etc. Furthermore, these gene polymorphisms can be defected simultaneously after multiplex PCR and hybridization at one DNA chip.

The distribution of the −1143G>T, −1400C>T, −1453T>C, and −1454insC polymorphisms, verification of haplotypes and use of these genotypes were investigated for finding further relevant polymorphisms and haplotypes.

For that, different DNA samples of Caucasians (n=205) were genotyped. The result is shown in the following table:

| SNP | Genotypes | | |
| --- | --- | --- | --- |
| −1143G > T | GG: 136 | GT: 65 | TT: 4 |
| −1400C > T | CC: 44 | CT: 107 | TT: 54 |
| −1453T > C | TT: 102 | TC: 85 | CC: 18 |
| −1454insC | —: 102 | —C: 85 | CC: 18 |

Beside Caucasians, the genotype distributions in Black Africans were likewise investigated:

| SNP | Genotypes | | |
| --- | --- | --- | --- |
| −1143G > T | GG: 57 | GT: 40 | TT: 5 |
| −1400C > T | CC: 61 | CT: 38 | TT: 2 |
| −1453T > C | TT: 54 | TC: 38 | CC: 4 |
| −1454insC | —: 54 | —C: 38 | CC: 4 |

The genotype distributions in Chinese are shown in the following table:

| SNP | Genotypes | | |
| --- | --- | --- | --- |
| −1143G > T | GG: 72 | GT: 22 | TT: 4 |
| −1400C > T | CC: 37 | CT: 46 | TT: 16 |
| −1453T > C | TT: 30 | TC: 41 | CC: 15 |
| −1454insC | —: 30 | —C: 41 | CC: 15 |

A comparison of the genotype distributions in most cases resulted in significant differences between the ethnic groups. Such differences in the genotype distributions in different ethnic groups normally point out, that associated phenotypes were significant for evolution and provided the carriers with a certain advantage. It is known to the person skilled in the art that ethnically different genotype distributions are a reference to the fact that even today, certain genotypes and haplotypes are associated with certain diseases or physiological and pathophysiological modes of reaction or responses to treatment, e.g. with pharmaceuticals.

In one-hundred sequenced DNA samples of healthy Caucasians, further analyses showed a coupling imbalance between certain polymorphisms. Coupling imbalance means the occurrence of allele combinations (haplotypes), which statistically clearly occur more frequently or less frequently together, than this was to be expected in relation to their frequency. In that, it turned out that polymorphisms 1453T>C and 1454insC link up completely. Polymorphisms −1143G>T and −1440C>T, on the other hand, do not link up, and they only restrictedly couple with the two other variants (FIGS. 6A and B). The quality of the coupling is marked with the values $D'$ and $r^2$. In that, $D'=1$ and $r^2=1$ are considered a significant coupling. The closer both values are to 1, the narrower is the coupling imbalance. The calculation of the haplotypes, which can be constructed from those four polymorphisms, resulted in five different allele combinations. No preferential haplotype exists, which results from these promoter variants (FIG. 6C). In order to determine any possible combinations, the verification of at least three of the four polymorphisms is necessary.

One subject of the invention is that these new polymorphisms can be used to detect and validate further relevant genomic genetic modifications in CHK1 or neighboring genes, which for example are in coupling imbalance with genotypes in the CHK1 gene. These may also be genes, which are likewise located on chromosome 11, but far away from the CHK1 gene. For that, the procedure is as follows:

1. For certain phenotypes (cellular characteristics, diseases, progression of diseases, drug responses, etc.), an association with the polymorphisms 1453T>C, 1454insC, −1143G>T and −1400C>T is first established, whereat these associations can be established for each genotype individually or using all permutations of the haplotypes.
2. For newly detected genetic modifications in CHK1 or neighboring genes it is investigated, whether already existing associations are enhanced or weakened using the genotypes or haplotypes described above.

Functional Significance of the Promoter Polymorphisms in the CHK1 Gene

It was investigated, which functional changes are to be allocated to the promoter polymorphisms in the CHK1 gene. Perceivable here are, for example, a correlation to alternative splicing, tissue-specific expression or an over-expression of the CHK1 protein depending on genotypes or haplotypes, respectively, of the CHK1 promoter. For that, it was first investigated using a computer program, whether the nucleotide exchanges found can influence the binding of transcription factors. Transcription factors bind to specific consensus sequences and can increase or reduce the promoter activity, so that an enhanced or reduced transcription of the gene results and thus the expression level of the coded protein is increased or reduced. As shown in FIG. 7, all promoter SNPs mentioned above are located in a consensus sequence for binding sites of different transcription factors (e.g. E74A, CF2-II or bZIP910), the binding of which can be effected by the polymorphisms. The occurrence of certain genotypes results in an omission of these binding sites by the modification of their consensus sequences. For experimental investigation of this effect, a so-called EMSA (electrophoretic mobility shift assay) is performed. In this test, short nucleic acid sections, which include the respective polymorphism, are incubated with cell nucleus extracts. Transcription factor proteins present in these extracts now bind to the nucleic acid sections with different intensity. The binding to the DNA is finally made visible on the X-ray film. In that, an intensive band results from a strong bond. FIG. 8 shows the result of this test with specific constructs, which either contain the G- or the T-allele of the −1143G>T polymorphism. The presence of the G-construct band proves binding of a transcription factor to this region. The T-construct has no band, which shows that no transcription factor binds to this allele. The weakening of the band intensity by a specific oligonucleotide shows, that the binding transcription factor is a specific binding. FIG. 9 shows the result of this test with specific constructs, which either contain the C- or the T-allele of the −1400C>T polymorphism. Only the T-construct results in the binding of a transcription factor, while the C-construct shows no specific band, therefore also no transcription factor binds to this allele. The displacement of the band by a specific oligonucleotide shows that the binding transcription factor is a specific binding.

For functional verification of a regulatory activity of these promoter regions, depending on certain genotypes, different fragments of the promoter were cloned into the vector pSEAP to quantify the regulatory activity using a so-called reporter assay following the expression of the vector in HELA cells, a cervix carcinoma cell line (FIG. 10). For that, the constructs are cloned in front of a gene, which codes for secreted alkaline phosphatase (SEAP). If the construct has a gene-regulating activity, the transcription of the SEAP gene is increased and the increased secretion of alkaline phosphatase into the cell culture medium is measurable. As shown in FIG. 10, the constructs with the alleles of the −1143G>T polymorphism have a significantly higher activity than the constructs of the other polymorphisms (p=0.0005). The reporter activity of the individual alleles of this SNP is likewise different. The T-allele shows a higher activity (3.82±0.6) than the G-allele (2.36±0.3).

Since only the −1143G>T polymorphism of the CHK1 gene shows a reporter activity, next it was investigated, how the regulation in vivo takes place, because reporter assays are an artificial cell system. For that, the expression of CHK1 at the mRNA level was investigated using real-time PCR in human tissue.

For that, mRNA was obtained from human surgery tissue from urinary bladder and colon surgeries and transcribed into cDNA using reverse transcriptase. The person skilled in the art is familiar with this method. Subsequently, the expression level was determined using real-time PCR (Taqman method) and matched with the expression level of the housekeeping gene .beta.-actin. The results are shown in FIGS. 11 and 12. It is shown in section 11A, that the GG-genotype of the −1143G>T SNP has a significantly higher mRNA expression than the TT-genotype. The values of the heterozygote genotype are located in-between, which indicates a gene dosage effect. FIG. 12A, too, shows an increased mRNA expression for the GG-genotype. The two other polymorphisms also show an allele-dependent difference in the gene expression. As FIGS. 11B and 12B illustrate, C-allele carriers of the −1400C>T polymorphism have clearly more CHK1 mRNA than carriers of the TT-genotype. The real-time PCR results for the SNPs −1453T>C and 1454insC are shown in FIGS.

11C and 12C. Carriers of the T-allele, which do not have an additional insertion, show a clearly lower mRNA expression.

Using this method, it was verified that there are genetic modifications in the CHK1 gene, which effect a change of expression of CHK1 in the carcinoma tissue. This can be the promoter polymorphisms described above or polymorphisms in coupling imbalance with these SNPs. One component of the invention described here is thus also to quantify the expression of CHK1, to associate it with known polymorphisms of CHK1 and to discover and validate new, even better suitable polymorphisms.

The findings of a genotype-dependent expression of CHK1 in human carcinoma tissue shown here are exceedingly significant, since a lower activity of CHK1 can cause microsatellite and chromosomal instability, which both are included in the characteristics of genomic instability and thus favor oncogenesis and have a negative effect on tumor progression (Durkin et. al., Depletion of CHK1, but not CHK2, induces chromosomal instability and breaks at common fragile sites. 2007, Oncogene 25:4381-8; Furlan et al., Genetic progression in sporadic endometrial and gastrointestinal cancers with high microsatellite instability. 2002, J. Pathol. 197:603-9). Furthermore, this genotype-dependent gene expression of CHK1 can also affect the response to treatment with CHK1 inhibitors. It has to be expected that a low gene expression predisposed by a certain genotype, e.g. the TT-genotype of the −1143G>T polymorphism, responds stronger to CHK1 inhibitors than other genotypes. Thus, genetic modifications in the CHK1 gene can be used to predict the response to a cancer treatment to discriminate, for example, responder versus non-responder. These genetic modifications can also be used for dosage finding or for predicting the occurrence of undesired drug effects, respectively. Such cancer treatments can take place as drug treatments in the broadest sense, i.e. by supplying substances into the body, or these cancer therapeutic agents can have a physical effect (radiation, warmth, cold).

We thus expect an influence on the progression of diseases, in particular in case of tumor diseases, as well as a changed response to substances, which influence the regulation cascade of CHK1, or substances, which directly inhibit CHK1.

Use of Genetic Modifications in CHK1 for Predicting Disease Risks and Progression of Diseases Due to the key function of checkpoint kinase 1 for the regulation of the cell cycle, it is an essential component of the invention that using genetic modifications in CHK1, disease risks and progression of diseases can be generally predicted.

The multistep development of cancer reflects the accumulation of genetic modifications, which result in the transformation of normal cells into cancer cells and of normal tissue to benign and possibly malignant, invasive tumors. The accumulation of alterations in tumor suppressor genes and proto-oncogenes accelerates tumorgenesis and can influence radio—as well as chemotherapy. However, it becomes more and more clear that disturbed DNA repair mechanisms as well as checkpoints are the reason for the increased genomic instability of tumors (Hoeijmaker J. H., Genome maintenance mechanisms for preventing cancer. 2001 Nature, 411:366-74; Khanna et al., DNA double-strand breaks: signaling, repair and the cancer connection, 2001, Nat. Gent. 27:247-54). Since checkpoints play a central role in the maintenance of genomic integrity, it has to be directly expected that the progression of varied and completely different tumor diseases with a genetically determined, reduced activatability is influenced by checkpoints. That means that with changes in the expression of proteins, which are expressed in all human body cells and protect the cell from DNA damage, cell functions are regulated, which decisively influence or at least modulate all physiological and pathophysiological processes. Besides that, responses to pharmaceuticals are also influenced in a particular manner. This affects desired, but also undesired drug effects.

It was repeatedly postulated in the scientific literature that functional modifications of checkpoint proteins have a sustained influence on varied diseases or on the progression of varied diseases, respectively, since these are phylogenetically highly conserved pathways. Such genetic modifications can be structure-modifying mutations in the checkpoint proteins, which, for example, reduce the activation of the proteins by phosphorylation or the substrate selectivity. Furthermore, the expression level can be modified, whereby the initiation of the subsequent reaction cascades, which e.g. induce apoptosis, is reduced, or splicing variants with a changed function can occur. All these modifications are considered a genetic predisposition for cancer.

The following results from the examples stated:
1. Genetic modifications in genes coding for ubiquitarily expressed proteins influence varied diseases or cause varied disease risks, respectively.
2. Checkpoint proteins are part of the complex network for maintaining the genomic integrity in the human body.

Diseases accompanied by a genetic modification in CHK1 and determined, for example, by a changed level of expression of the CHK1 protein, are benign neoplasias of any tissue of origin and malignant neoplasias of any tissue of origin.

Such neoplasias comprise, for example, tumor diseases like tumors of the urogenital tract: urinary bladder carcinoma, kidney cell carcinoma, prostate carcinoma and seminoma;
tumors of the female genitals: mammary carcinoma, corpus carcinoma, ovarian carcinoma, cervix carcinoma;
tumors of the gastrointestinal tract: oral cavity carcinoma, esophagus carcinoma, stomach carcinoma, liver carcinoma, bile duct carcinoma, pancreas carcinoma, colon carcinoma, rectum carcinoma;
tumors of the respiratory tract: larynx carcinoma, bronchial carcinoma;
tumors of the skin: malignant melanoma, basalioma, T-cell lymphoma;
tumor diseases of the hematopoietic system: Hodgkin and non-Hodgkin lymphomas, acute and chronic leukemias, plasmocytoma;
tumor diseases of the brain or the nerve tissue, respectively: glioblastoma, neuroblastoma, medulloblastoma, meningeal sarcoma, astrocytoma;
soft tissue tumors: for example sarcomas and head-neck tumors.

Use of Genetic Modifications in the CHK1 Gene for Predicting Progression of Diseases and Response to Treatment Since the essential functions of CHK1 are known, genetic modifications in the CHK1 gene can increase the risk for tumor diseases or influence the progression of diseases. It is generally impossible to investigate all human tumor diseases and their progression. However, we have demonstrated this here by way of example for five different carcinomas: urinary bladder carcinoma, colorectal carcinoma, chronic lymphatic leukemia, malignant melanoma and cholangiocellular carcinoma. These data clearly prove the usability of genetic modifications in the CHK1 gene for the purpose described here. These diseases are a priori not associated at all.

The Significance of Checkpoint Kinase 1 for Chemotherapeutic Agents and Radiation Genetic instability is a characteristic of all tumors and also plays a role in oncogenesis, progression and the development of resistances against pharmaceuticals (Hartwell L., Defects in a cell cycle checkpoint may be responsible for the genomic instability of cancer cells. 1992, Cell 71:543-6). Most tumor cells have a defective G1-S checkpoint, which gives them a survival advantage. This defect, however, causes the tumor cells to depend on the G2 checkpoint very much, if stimuli are present, which threaten the genomic integrity. The inhibition of the G2 checkpoint by administration of DNA-damaging substances can result in a so-called "mitotic catastrophe", i.e. cell death. CHK1 is responsible for the maintenance of the G2 checkpoint, if DNA damage occurs. Thus, the inhibition of CHK1 by the omission of the G2 checkpoint offers the possibility, that DNA damages and modifications caused by genotoxic substances and radiation can accumulate and that the tumor cell dies of it. This, however, requires that the inhibition of CHK1 does not promote somatic cell death, which would mean general cellular toxicity and little tumor specificity. The use of CHK1 siRNA in vitro has shown that CHK1 inhibition has only little influence on the cell cycle and the survival of the cell, as long as no DNA-damaging substances are present. Upon using these substances, however, the G2 checkpoint is securely inhibited and the apoptosis increased. Since the discovery and development of the CHK1 inhibitors, it could be verified, that by using them, the effect of chemo- and radio-therapeutic measures could be increased.

If genetic modifications occur in CHK1, which influence the gene expression, then this has an impact on the effectiveness of these CHK1 inhibitors. It has to be expected, that patients with a genotype-dependent lower CHK1 expression respond better to the inhibitors than patients with a higher CHK1 expression. Additionally, it means that the combined treatment of CHK1 inhibitors with chemo- and immunotherapeutic agents and/or radiation can be influenced. From this results the possibility of individual diagnostics of the general responsiveness to these cancer therapeutic agents and therapy measures as well as an individual prediction of the risk of undesired effects by these therapies.

Genotype-Dependent Diagnostics of the Expression of CHK1 Enables General Diagnostics of the Effectiveness of Chemotherapeutic Agents and Radiation, Their Optimal Dosage and the Occurrence of Side-Effects.

Chemotherapy uses such substances, which exert their damaging effect on certain cancer cells as targeted as possible and kill them or inhibit them in their growth. A certain cytostatics dosage can always only kill a certain portion of the target cells, which remains the same with proceeding treatment. Therefore, chemotherapy must not be reduced within the course of the treatment, even if the tumor is not even detectable anymore. It rather has to be assumed, that with a weak treatment, especially the resistant tumor cell clones are selected. Chemotherapy is applied in fast succession, and almost always two or more cytostatics are combined to increase effectiveness. The therapy thus also causes side-effects, which are classified according to the common toxicity criteria. These criteria include: number of leukocytes and thrombocytes, sickness, vomiting, diarrhea and stomatitis.

Radiotherapy means the use of ionizing high-energy radiation to heal malignant tumor diseases. Such malignant tumors are often also treated in combination with chemo- and radiotherapy. A multitude of tumor diseases can thus also be healed in advanced stages. In order to keep the side-effects low, the radiation is divided into many daily single doses and administered over several weeks. Still, side-effects like redness, sickness, diarrhea, or hair loss occur, depending on the dosage, penetration depth and number of single doses. The invention is now based on the fact that a method has been developed, which is generally suited for diagnostics of the activatability of checkpoint kinase 1 and, associated with it, the G2 checkpoint. For that, one or more polymorphisms in the CHK1 gene are investigated. With high expression, there predictably is an increased activatability of the G2 checkpoint and thus sufficient time to perform repair mechanisms in the DNA after damaging of the same. With low CHK1 expression, the G2 checkpoint is less activatable and DNA damage is not or not sufficiently repaired.

In order to verify by way of experiments, that there is a connection between CHK1 polymorphisms and the activity of the G2 checkpoint, and thus also with DNA repair mechanisms, lymphocytes of healthy subjects were cultivated and stimulated for cleavage. After 72 hours, these cells were radiated with a dose of 1 Gy and subsequently arrested in the M-phase by the mitosis inhibitor colchicine. From these cells, chromosomes were prepared using methods the person skilled in the art is familiar with and, depending on the −1143G>T polymorphism, evaluated for damage by radiation in 50 metaphases each. In this manner, only those cells were included into the evaluation, which at the time of radiation were in the G2-phase and until the chromosome preparation reached the M-phase. Thus, with this method, the activity of the G2/M checkpoint can be assessed. As shown in FIG. 13, the average number of chromosome breaks per metaphase for the GG-genotype was 2.7, for the GT-genotype 4.1, and for the TT-genotype 4.9 (p=0.031). Thus it could be demonstrated, that with the GG-genotype, which forms the most mRNA, the G2/M checkpoint is the most active and the respective DNA repair mechanisms could work best. The weak checkpoint for the TT-genotype, on the other hand, allows only few repair mechanisms to work, and more damage can accumulate.

Thus, a determination of the presence of polymorphisms in CHK1 allows for diagnostics of the effectiveness and undesired effects of drugs, in particular cytostatics, as well as other forms of treatment, which damage the genetic make-up of the tumor cells, e.g. radiation. Besides that, such polymorphisms in CHK1 can be used to diagnose the effects of pharmaceuticals used in combination with a CHK1 inhibitor. Additionally, the diagnostics of the allele or haplotype status in CHK1 can be used to determine the individually optimal and tolerated dosage of drugs. For diagnostics of an increased or reduced activatability of checkpoint kinase 1 and the G2 checkpoint serves in particular the verification of the CHK1 promoter polymorphisms described here, either alone or in any perceivable combinations.

Besides that, any further genetic modifications in CHK1 can be used for diagnostics, which are in a coupling imbalance to these polymorphisms and/or additionally promote or inhibit the alternative splicing process or the expression.

These genetic modifications can be verified with the methods described above, which the person skilled in the art is familiar with. Furthermore, these gene polymorphisms can be simultaneously detected after multiplex PCR and hybridization to a DNA chip. Besides that, other methods may also be used for diagnostics, which allow for the direct verification of the expression level of CHK1 or splicing variants of CHK1.

The method stated is particularly suited for diagnostics of the effect of substances, which damage the DNA of the tumor cells. These substances include oxaliplatin, 5-fluorouracil, folinic acid, irinotecan, capecitabine and cisplatin, whereat, the list could be randomly extended. Besides that, the effects of immunotherapeutic agents (e.g. interferons or interleukins) or inhibitors of signal transduction in tumor cells, respectively, can be predicted.

Furthermore predicted can be the effects of radio-therapeutic measures, like gamma radiation, X-ray radiation, electrons, neutrons, protons and carbon ions, whereat the list could be randomly extended. In the broader sense, radiation therapy also implies the medical application of microwaves and heat rays, light and UV therapy as well as the treatment with ultrasound radiation.

A proof for the general usability of the CHK1 polymorphisms for predicting drug effects results from the genotypes observed and their dependent progression of diseases in the examples stated above. Patients, the tumors of which were intensively treated with chemo- or radiotherapy, respectively, show a more favorable progression of the disease, if, genotype-dependent, they show less CHK1 expression. With the lower quantify of CHK1 protein, the G2 checkpoint is less activatable and cytostatics or radiation, respectively, can have a more effective effect. On the other hand, the disease progresses more favorable in tumor patients, who received other therapeutic measures, if they, depending on the genotype, show more CHK1 expression. With the higher quantity of CHK1 protein, the G2 checkpoint is more active and can thus contribute to DNA repair mechanisms and limit the genomic instability of the tumor.

A substantial subject of the invention is the provision of diagnostically relevant genetic modifications in the CHK1 gene as prognosis factor for all human tumor diseases. Naturally, not all tumor diseases can be described in that. The principle will therefore be further explained in selected examples, which demonstrate general usability without restricting the scope of patent to the exemplary embodiments.

EXAMPLES

Example 1

Urinary Bladder Carcinoma

Bladder cancer is a malignant tumor of the mucous membrane of the urinary bladder and most frequently occurs between the age of 80 and 70. Men are affected by it three times as often as women. In men, bladder cancer is the third most frequent type of cancer after lung and prostate cancer. Bladder cancer can be caused by external influences. The risk factors include smoking, permanent strain on the organism by chemicals, like for example colorants or analgesic misuse. In many patients, the examinations show that it is a superficial tumor. This can be removed by surgery using a cystoscope. More than 70% of the patients treated because of a superficial bladder carcinoma show tumor rescrudescence in progression. In that, in more than half the patients, rescrudescence tumors with non-muscle-invasive disease occur. These can be curatively treated or controlled, respectively, by transurethral resection. It is therefore important to detect these lesions early and to provide regular and closely monitored aftercare for the patients. At regular intervals, excretion urograms serve to control possible tumor manifestations in the renal pelvis and ureters. So far, there are hardly any valid markers predictive for the further progression of the disease. Therefore, currently the classic factors like penetration depth, degree of differentiation, formation of metastases, involvement of the lymph nodes, etc, are used for prognosis. Genetic markers for probability of survival and therapy response would substantially improve the care for patients with urinary bladder carcinoma. It is the object of the invention to demonstrate that the use of genetic modifications in CHK1 is suited to predict the further progression of the disease.

FIG. 14A shows the survival depending on the −1143G>T SNP. In that, the risk of dying in patients with the TT-genotype is increased by approx. the 2-fold (p=0.042). The median time until death is only 48 months for carriers of the TT-genotype, while for G-allele carriers, no median time can be stated, since up to the end of the study, less than half of these patients died. A similar relation is found, if only the survival of the older patients is investigated (FIG. 14B). The progression of the curve is significantly different for the genotypes (p=0.004), whereat the G-allele carriers are allocated the more favorable progression. The median time of survival is 87 months (GG-genotype) or 50 months (GT-genotype), respectively, in patients with the G-allele; for the homozygous T-allele carriers, on the other hand, only 33 months.

Example 2

Colorectal Carcinoma

The colorectal carcinoma is the most frequent type of tumor in the gastrointestinal tract and one of the main causes for tumor-related death worldwide (12-15% of the total cancer mortality). In Germany, the incidence is about 51,000 new cases per year. The average 5-year survival rate after tumor resection is only approx. 50%. Eating habits, cancer-promoting metabolites, exogenous carcinogens and certain predisposing diseases are included in the risk factors for the formation of a colorectal carcinoma. The standard method for predicting the progression of the disease is the TNM or UICC stage system, respectively. Patients with UICC stages III or IV generally have a worse prognosis than patients with UICC stages I or II. An adjuvant chemotherapy is performed for metastasized colorectal carcinomas (UICC stages III and IV) and can enhance the local effect of radiation therapy. A majority of these patients develops recrudescences or metastases, which makes intensive aftercare necessary. Thus, it is important to identify and establish molecular markers, which can predict the further progression of the disease. A further component of the invention consists in using genetic modifications in CHK1 to predict the further progression of the colorectal carcinoma.

FIG. 15A shows a significant difference in regards to survival depending on the −1143G>T polymorphism (p=0.026). Patients with the GG-genotype in median survive 26 months, whereas in the T-allele carriers, less than half the patients died during the observation period. Additionally, a gene dosage effect is detectable, since carriers of the heterozygous genotype have a higher risk than the TT-genotype and a lower risk than the GG-genotype. FIG. 15B shows, depending on the −1400C>T SNP, the survival of the patients with tumor localization in the colon. Carriers of the TT-genotype survive significantly longer than carriers of the C-allele (p=0.033). While the median survival for the TT-genotype is 70 months, it is only 34 months for the CT-genotype and only 26 months for the CC-genotype. Depending on the genotypes of the polymorphisms 1453T>C and 1454insC, a significant difference in regards to survival can likewise be detected (FIG. 15C). Patients, who have the TT-genotype at position 1453 and have no insertion at position 1454 survive longer than patients, who have the 1454C allele and the insertion (p=0.007). The median survival is 70 months for the TT-genotype without insertion compared to 21 and 15 months for the other genotypes.

Above all interesting here is the observation, that patients with a low CHK1 mRNA expression, since they are carriers of the TT-genotype, survive the longest. Since patients with UICC stages III and IV, who constitute the biggest portion of this collective, received intensive treatment against their tumors, the circumstance to survive longer, if one has little CHK1 protein, is of high significance. Reduced CHK1 may be considered a predisposition for tumor diseases; however, it also makes the tumor cells more susceptible to therapeutic measures. This is confirmed by the curves of survival shown here.

Example 3

Chronic Lymphatic Leukemia

Chronic lymphatic leukemia (CLL) is a chronic form of leukemia. Characteristic for the disease is a high number of abnormal lymphocytes. A total of 30 percent of all leukemic diseases are chronic lymphatic leukemias. The median disease age is 65 years. A CLL can be benign for up to 20 years, i.e. the patients show no symptoms except for enlarged lymph nodes, tiredness and lack of appetite. The treatment only starts, if the number of lymphocytes highly increases, the portion of erythrocytes and thrombocytes decreases, or other complications occur. An early treatment has no influence on the progression of the disease. The most important therapeutic measure is chemotherapy. The further the disease has progressed, the higher are the disturbances of health by the modification of the organ system. Depending on the Binet stage of the disease, the doctor can estimate the prognosis. The stage of a CLL is, among others, characterized by how many lymphocytes are present in blood and bone marrow, how large spleen and liver are and whether an anemia is present. A CLL results in modifications in the immune system, so that humans suffering from this disease have a higher risk of developing other types of cancer. At the same Binet stage, however, patients show a completely different progression of the disease. It is an object of the invention to demonstrate that genetic modifications in the CHK1 gene are suited to predict the progression of CLL.

For that, patients with CLL were genotyped in regards to the described genetic modifications in CHK1 and the gene status was associated with survival. FIG. 16 shows the survival depending on the −1143G>T genotype. Patients, who are carriers of the T-allele, survive longer than patients, who are homozygous GG. For the GG-genotype, the median survival is 146 months; on the other hand, however, less than half the patients carrying the T-allele died during the observation period. Here, too, if shows that under intensive treatment, a genotype, which results in a low CHK1 expression, is most favorable for survival.

Example 4

Malignant Melanoma

The malignant melanoma is a malignant abnormality of the melanocytes (pigment cells of the skin), which is why it is also called "black skin cancer". This type of tumor tends to spread metastases via the blood and lymph streams very early. The incidence of malignant melanoma is increasing, it doubles every 15 years. Particularly at risk are persons with low pigmentation. The risk factors include, above all, intensive sun exposure and a sunburn anamnesis of 5 or more episodes in the youth. In the Western world, malignant melanoma is the most frequent cancer in women between the age of 20 and 40. Criteria for prognosis and therapy are provided by the stages of the TNM classification, the tumor thickness according to Breslow, the penetration depth according to Clark, the differentiation by subtypes and localization. With early diagnosis and treatment, the prognosis still is good. With late diagnosed melanomas with lymph node metastases, the 5-year survival rate lies at approx. 30%; if remote metastases are present already, it is only 0-5%. There are no molecular markers for the progression of this disease and responses to treatment. The identification of such markers would highly improve the pre- and aftercare of the patients.

FIG. 17A shows the genotype-dependent difference of the −1400C>T SNP from the time of initial diagnosis and initial treatment up to the time of requirement of further treatment. Patients carrying at least one C-allele, start continuative treatment significantly later than patients with the TT-genotype (p=0.033). For the heterozygous or homozygous, respectively, C-allele carrier, treatment becomes necessary in median after 71 or 57 months, respectively, and for the TT-genotype after 45 months already. Contrary to the curve progressions discussed so far, here it shows that without medical measures, those genotypes are advantaged, which have a high CHK1 expression and thus very well working checkpoints. FIG. 17B represents the survival of all patients. Here, too, it can be recognized that patients carrying at least one C-allele survive longer than patients with the TT-genotype (p=0.013). The median survival for the TT-genotype is only 69 months, for the CC-genotype, on the other hand, 101 months, and the heterozygous genotype does not even reach the median survival time during the observation period. For this type of tumor, the treatment of the primary tumor is a completely surgical one. After the excision of the tumor, further treatment is considered. In 76.5% of the patients, there was no further treatment, 11.2% received an immune therapy with interferon-$\alpha$, 3.4% a hyper-thermal extremities perfusion, in 5.4%, a re-resection was necessary and the remaining 3.5% were subjected to other therapeutic measures. Since only 1.6% of the patients received a chemo- and/or radiotherapy, which would be favored by a low CHK1 expression, here those genotypes are advantaged, which have a strong CHK1 expression (real-time PCR results from FIG. 12B: CC- and CT-genotype 0.009±0.002, TT-genotype 0.004±0.002, p=0.049) with a strongly working checkpoint kinase 1.

Example 5

Cholangiocellular Carcinoma

The cholangiocellular carcinoma (CCC) is a malignant tumor of the bile ducts of the liver. Compared to Asia and Africa, where it represents the most frequent type of tumor with 20-30% of the malignant tumors, it is relatively seldom in Central Europe (<1% of all malignant diseases). The risk factors include colitis ulcerosa, chronic bile duct inflammations and viral hepatitides. The curative treatment of a CCC is a partial liver resection or a total hepatectomy with liver transplantation. The recrudescence rate is very high. The prognosis for CCC is therefore very unfavorable, in particular in patients with non-resectable tumors, who have a 5-year survival rate of <10%. The median survival period in patients with non-resectable CCC is 6 to 10 months. So far, no molecular markers are known for the progression of this disease, however, would substantially improve the care for patients with CCC. It is therefore a component of the invention to demonstrate that the use of genetic modifications in CHK1 is suited to predict the further progression of the disease.

FIG. 18 shows the survival of CCC patients. Patients with the CC- and CT-genotypes survive significantly longer than patients with the TT-genotype (p=0.036). The median survival of the TT-genotype is 5 months, that of the other genotypes 9 months. Since the probability of survival of the CCC patients is only very low, the time for an intensive treatment after the surgery is very short. Due to the mostly pre-damaged cirrhotic liver, the indication for radiotherapy is given only rarely; additionally, the liver is extremely radiosensitive. Thus, until achieving a tumoricidal dose, the liver might already be destroyed. So far, systemic chemotherapy with numerous cytostatics and combinations has not shown lasting effectiveness. The remission rates are 20 to 30%, the median duration of remission is 4 to 6 months. Alternatively, chemoembolizations or targeted intratumoral alcohol injections can be applied. Since for CCC neither radio—nor chemotherapy can be used to a sufficient extent, which for a low CHK1 level would show advantages, for this type of tumor, it is the genotypes showing an increased CHK1 expression, which show longer survival.

Example 6

Mammary Carcinoma

The mammary carcinoma is the most frequent tumor of the female population in Europe and the USA. It affects 7-10% of all women and accounts for 25% of the total female cancer mortality. The etiology of the mammary carcinoma is still unknown, however, risk factors have been described, like a family disposition, radiation exposure or estrogen influence. In most patients, the examinations show that it is an invasive carcinoma. With a few exceptions, any operable mammary carcinoma even with verified remote metastatization is treated surgically. The differently radical initial surgical treatment results in variations of the locoregional recrudescence rate, but not the long-term chance for survival. Furthermore, recrudescences or remote metastases quite often can become manifest after 5 or even 10 years only. It is therefore important to detect these lesions early and to closely monitor the patients in aftercare. Aftercare examinations are performed at regular intervals, with an interim suspicion even up to 10 years after surgery. So far, there are hardly any valid markers predictive for the further progression of the disease. Therefore, currently the classic factors like tumor size, metastatization, involvement of lymph nodes, hormone receptor status, etc. are used for prognosis. Genetic markers for probability of survival and therapy responses would substantially improve the care for patients with mammary carcinoma. It is an object of the invention to demonstrate that the use of genetic modifications in CHK1 is suited to predict the further progression of the disease.

FIG. 19 shows a significant difference in regards to the survival depending on the −1143G>T polymorphism (p=0.017). Patients with the GG-genotype survived in median 87 months, whereas for the patients with the GT-genotype the median survival time is 101 months. Contrary to that, in homozygous T-allele carriers, less than half the patients died during the observation period.

Here, above all the observation is interesting again, that patients with a low CHK1-mRNA expression, since they are carriers of the TT-genotype, survive longest. Besides a possible hormone therapy, patients with mammary carcinoma in most cases receive an adjuvant radio- and/or chemotherapy. That means that a reduced CHK1 protein quantity in association with such a treatment strategy results in longer survival of the patients.

Other Diseases

While the examples represented here exclusively relate to cancer diseases, if still has to foe emphasized that proliferation processes, apoptosis and cellular modification occur with all human diseases and that thus DNA repair mechanisms and DNA checkpoints play an important role in these processes. For example, a heart attack develops on the basis of vascular changes of the coronary arteries, in which proliferative processes play an important role. The recovery of the myocardium, too, requires such modification processes after the infarct. The same applies to the brain after an ischemic infarct. Insofar, one or more of the genetic modifications described here can thus be used to predict the progression of cardiovascular diseases. For infectious diseases, like e.g. with the hepatitis virus, such proliferation processes take place as well, which, for example, can result in cirrhosis in the liver. Insofar, one or more of the genetic modifications described here can thus be used to predict the progression of infectious diseases. For neurodegenerative diseases, e.g. Alzheimer disease or multiple sclerosis, too, growth and cellular modification processes play an important role.

The invention claimed is:

1. A method of treating a urinary bladder carcinoma of a patient, comprising:
   (a) predicting a response of the carcinoma of the patient to a cancer treatment, comprising: (i) obtaining a DNA sample of the patient; (ii) detecting the patient's genotype at position −1143 of the checkpoint kinase 1 promoter; and (iii) predicting survival of the patient, wherein the presence of a G allele at the position predicts increased survival and the TT genotype at the position predicts decreased survival, and
   (b) treating the patient with chemotherapy, radiotherapy, or a combination of both.

2. A method of treating a colorectal carcinoma of a patient, comprising:
   (a) predicting a response of the carcinoma of the patient to a cancer treatment, comprising: (i) obtaining a DNA sample of the patient; (ii) detecting the patient's genotype at positions −1143, −1453, and −1454 of the checkpoint kinase 1 promoter; and (iii) predicting survival of the patient, wherein the presence of a T allele at position −1143 predicts increased survival and the GG genotype at position −1143 predicts decreased survival, and the presence of a T genotype at −1453 and no insertion at −1454 predicts increased survival and the presence of the C allele at −1453 and the insertion at −1454 predict decreased survival, and
   (b) treating the patient with chemotherapy, radiotherapy, or a combination of both.

3. A method of treating chronic lymphatic leukemia of a patient, comprising:
   (a) predicting a response of the chronic lymphatic leukemia of the patient to a cancer treatment, comprising: (i) obtaining a DNA sample of the patient; (ii) detecting the patient's genotype at position −1143 of the checkpoint kinase 1 promoter; and (iii) predicting survival of the patient, wherein the presence of a T allele at the position predicts increased survival and the GG genotype at the position predicts decreased survival, and
   (b) treating the patient with chemotherapy, radiotherapy, or a combination of both.

4. A method of treating a cholangiocellular carcinoma of a patient, comprising:
   (a) predicting a response of the carcinoma of the patient to a cancer treatment, comprising: (i) obtaining a DNA sample of the patient; (ii) detecting the patient's genotype at position −1400 of the checkpoint kinase 1 promoter; and (iii) predicting survival of the patient, wherein the presence of a C allele at the position predicts increased survival and the TT genotype at the position predicts decreased survival, and
   (b) treating the patient with chemotherapy, radiotherapy, or a combination of both.

5. A method of treating a malignant melanoma of a patient, comprising:
   (a) predicting a response of the carcinoma of the patient to a cancer treatment, comprising: (i) obtaining a DNA sample of the patient; (ii) detecting the patient's genotype at position −1400 of the checkpoint kinase 1 promoter; and (iii) predicting survival of the patient, wherein the presence of a C allele at the position predicts increased survival and the TT genotype at the position predicts decreased survival, and
   (b) treating the patient with chemotherapy, radiotherapy, or a combination of both.

* * * * *